(12) United States Patent
Jönsson

(10) Patent No.: US 6,511,461 B2
(45) Date of Patent: Jan. 28, 2003

(54) NEEDLE HOLDING DEVICE

(75) Inventor: Jörgen Jönsson, Sjobo (SE)

(73) Assignee: Gambro Lundia AB, Lund (SE)

( * ) Notice: Subject to any disclaimer, the term of this patent is extended or adjusted under 35 U.S.C. 154(b) by 9 days.

(21) Appl. No.: 09/737,444

(22) Filed: Dec. 13, 2000

(65) Prior Publication Data

US 2001/0005780 A1 Jun. 28, 2001

(30) Foreign Application Priority Data

Dec. 22, 1999 (SE) .............................. 9904783

(51) Int. Cl.[7] ................................ A61M 5/31
(52) U.S. Cl. ...................... 604/240; 604/110; 604/192; 128/919; 206/364
(58) Field of Search .................. 604/240, 110, 604/162, 164.08, 192, 198; 128/919; 206/364, 365, 366

(56) References Cited

U.S. PATENT DOCUMENTS

| | | | |
|---|---|---|---|
| 4,617,012 A | 10/1986 | Vaillancourt | 604/29 |
| 4,654,034 A * | 3/1987 | Masters et al. | 604/192 |
| 4,725,267 A | 2/1988 | Vaillancourt | 604/192 |
| 4,804,371 A | 2/1989 | Vaillancourt | 604/198 |
| 4,874,384 A | 10/1989 | Nunez | 604/198 |
| 4,966,586 A | 10/1990 | Vaillancourt | 604/164 |
| 5,143,083 A * | 9/1992 | Al-Sioufi et al. | 128/63 |
| 5,285,896 A * | 2/1994 | Salaka et al. | 206/366 |
| 5,347,078 A * | 9/1994 | Eckels | 588/258 |
| 5,368,577 A | 11/1994 | Teoh et al. | 604/198 |
| 5,564,565 A * | 10/1996 | Yamada | 206/365 |
| 5,575,769 A | 11/1996 | Vaillancourt | 604/86 |
| 5,591,138 A | 1/1997 | Vaillancourt | 604/263 |
| 5,607,403 A * | 3/1997 | Kretzschmar et al. | 604/263 |
| 5,718,689 A * | 2/1998 | Stevenson | 604/192 |
| 6,059,758 A | 5/2000 | Padilla et al. | 604/263 |
| 6,123,193 A * | 9/2000 | Vojtasek et al. | 206/366 |
| 6,206,855 B1 * | 3/2001 | Kunkel et al. | 604/192 |

FOREIGN PATENT DOCUMENTS

GB 2343118 A 5/2000

* cited by examiner

Primary Examiner—Charles G. Freay
Assistant Examiner—Han L. Liu
(74) Attorney, Agent, or Firm—Peter B. Scull; Edna M. O'Connor; Laura M. Butterfield

(57) ABSTRACT

A needle holding device having an elongated hollow body with first and second ends, the first end being substantially open for receiving a needle. The hollow body also has a locking member operably disposed therein or thereon. The locking member has an opening to receive and non-releasably hold a needle inserted therethrough. Preferably, the locking member has one or more protrusions directed inwardly toward said opening, the protrusions being adapted to engage a needle in a locking relationship when the needle is inserted through the opening in the locking member. Also preferably, the needle holding device has an elastomeric sealing member operably connected to the hollow body, the elastomeric sealing member also being disposed adjacent the first end of said hollow body. The elastomeric sealing member is adapted to admit and seal around a needle pierced therethrough.

44 Claims, 7 Drawing Sheets

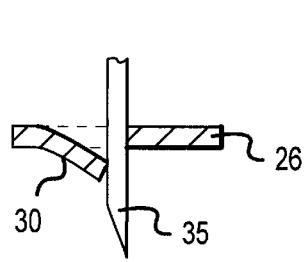
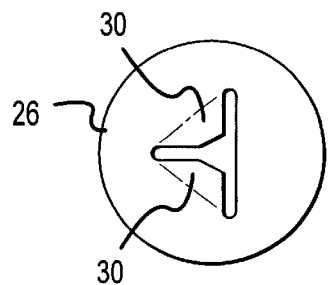
FIG.9  FIG.10
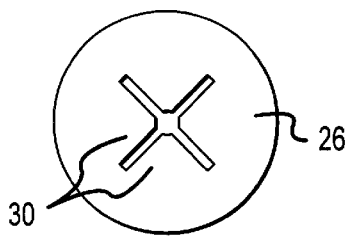
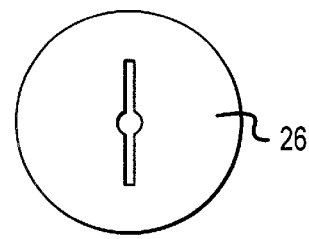
FIG.11  FIG.12
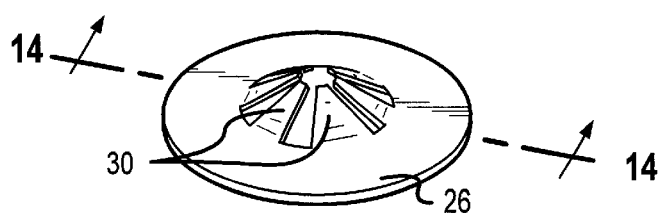
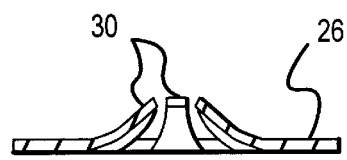
FIG.13  FIG.14
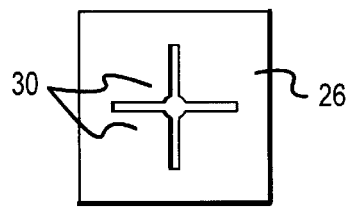
FIG.15

NEEDLE HOLDING DEVICE

FIELD OF THE INVENTION

The present invention is related generally to the field of devices used for holding medical needles after use. It is more particularly directed to such devices which lock the needle in an enclosure for safe needle disposal.

BACKGROUND

A particular area of concern for improved needle handling safety is in extracorporeal blood processing. In extracorporeal procedures, blood is removed from a patient, circulated through various tubing segments and one or more processing devices and then usually returned to the patient. Most often, the patient's blood is accessed via an access needle inserted in a patient vasculature access site, usually a vein or artery. In non-single needle systems, a second needle, also known as a return needle, is similarly inserted in a patient vasculature site, a return site, to return the processed blood to the patient.

Removal of these needles from the patient poses some significant safety concerns. Great care must be taken in the handling of these needles to prevent accidental needle sticks to the practitioner as well as to the patient. Bloodborne disease may be transmitted by such sticks. Moreover, caution must be exhibited relative to the vasculature access removal and return sites so that no damage is done thereto. This is particularly important for patients who routinely undergo extracorporeal treatments such as dialysis wherein the patient may be subjected to treatment as often as every other day. Repetitive needle insertion and removal this often requires a heightened degree of care to avoid vasculature damage so that the access removal and/or return sites are not rendered permanently inaccessible. During and after removal of the needle, manual pressure must be consistently applied to the access and return sites to arrest bleeding and achieve hemostasis thereby promoting natural closure and healing of the puncture opening. A practitioner preferably uses at least one hand to provide this continual manual pressure. Immediately upon needle removal, the practitioner will then also be concerned with using his or her other hand to safely secure the needle in a safety device for disposal.

Numerous devices have been introduced for improving the safety of handling used medical needles; both for syringes and for those needles, catheters or cannulas which may be connected to blood tubing sets or particular medical machines. However, many of these needle holding devices do not provide satisfactory security from the withdrawal of the needle from the device. Generally, if these contemporary devices provide a locking feature at all, it usually involves locking the needle hub or the elastomeric wings attached thereto. For example, three issued U.S. Patents disclose variations involving locking mechanisms like lock washers or analogous devices; namely, U.S. Pat. No. 4,874,384 issued to Nunez; U.S. Pat. No. 5,368,577 issued to Teoh et al.; and U.S. Pat. No. 5,575,769 issued to Vaillancourt. In these patents, the locking mechanism is directed either to gripping the needle hub (Nunez and Teoh) or the needle by way of mating dimples and protuberances (Vaillancourt). Nevertheless, the current art does not appear to provide for a solid, secure grip directly of any unmodified needle itself which would ensure that the needle will not escape from the needle holding device. Moreover, many other conventional needle holding devices are elaborate in design and thereby entail significant obstacles in manufacturing and use.

In view of the foregoing, it will be understood that improved, simply operated devices for securely locking used needles in safe enclosures for proper disposal are greatly needed in the art. It is toward satisfaction of these and other related desiderata that the present invention is directed.

SUMMARY OF THE INVENTION

The present invention is generally directed to a needle holding device having an elongated hollow body with first and second ends, the first end being substantially open for the insertion of a needle therein. A locking member is disposed in or on the hollow body adjacent the open first end. The locking member has an opening to receive and non-releasably hold a needle inserted therethrough. Preferably, the locking member has a plurality of inwardly directed protrusions such that the protrusions engage the needle in a locking relationship when the needle is inserted in and through the locking member opening. The needle holding device preferably includes an elastomeric sealing member operably connected to the hollow body also adjacent the open first end of the hollow body. The sealing member is adapted to admit a needle pierced therethrough.

In another embodiment, a needle holding device according to the present invention further comprises a second hollow body connected to the first hollow body, the second hollow body also having a substantially open end for receiving a needle; and also having a locking member disposed therein adjacent the open end of said second hollow body. The second locking member also has an opening to receive and non-releasably hold a needle inserted therethrough.

Still further embodiments involve needle holding devices in which the elongated hollow body is connected to a tubing segment or another tubing set component. For example, needle holding devices are included wherein the elongated hollow body of a needle holding device is connected to a drip chamber or to a dual drip chamber cassette. Dual needle holding devices are contemplated as connected to such components as well so that the two needles often used in extracorporeal procedures such as dialysis may both be simply secured for disposal after use.

These and other features of the present invention will be further illuminated in the following detailed description read in conjunction with the accompanying drawings which are described briefly below.

BRIEF DESCRIPTION OF THE DRAWINGS

In the drawings:

FIG. 9 is a cross-sectional view of an isolated portion of an alternative needle holding device according to the present invention;

FIG. 10 is a top plan view of the isolated portion of the alternative needle holding device shown in FIG. 9;

FIG. 11 is a top plan view of an alternative isolated portion of a needle holding device according to the present invention;

FIG. 12 is a top plan view of yet another alternative isolated portion of a needle holding device according to the present invention;

FIG. 13 is an isometric view of still another alternative isolated portion of a needle holding device according to the present invention;

FIG. 14 is a cross sectional view of the isolated portion of FIG. 13 taken along line 14—14 thereof;

FIG. 15 is a top plan view of yet still another alternative isolated portion of a needle holding device according to the present invention;

DETAILED DESCRIPTION

Figure 1:
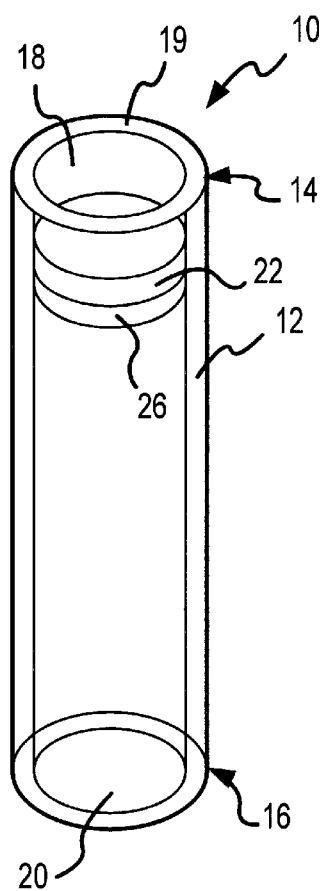
FIG. 1 is an isometric view of a needle holding device according to the present invention.

The present invention is directed generally toward needle holding devices and more particularly involves needle holding devices such as those shown in the attached drawings and identified generally by the reference numeral 10 therein. For example, as shown in FIG. 1, device 10 includes an elongated hollow body 12 which has first and second ends 14 and 16, respectively. First end 14 is generally open as shown by the opening 18 which is defined therein by a rim 19. Second end 16 is preferably closed which as depicted in FIG. 1 may be accomplished by having an end closure portion or bottom wall 20 integrally formed with a preferably impermeable body 12. The use of an impermeable body 12 and/or a bottom wall 20 is not necessary in all embodiments but both are preferred for preventing the escape of blood or other fluids from the interior of the device 10 as will be described in more detail below.

Figure 2:
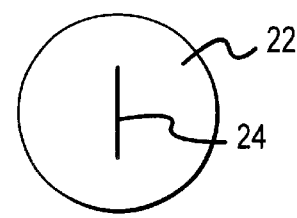
FIG. 2 is a top plan view of an isolated portion of the needle holding device of FIG. 1.

Also as shown in FIG. 1, device 10 preferably has an elastomeric sealing member 22 disposed in and adjacent the first end 14 of the hollow body 12. As shown, sealing member 22 is in contact with the locking member 26 and the inner side walls of body 12, although alternative dispositions of a sealing member 22 are contemplated as well as described below. This sealing member 22 may be a solid piece of elastomeric material or it may be a portion of elastomeric material having a slit 24 pre-defined therein as shown in the isolated view of sealing member 22 in FIG. 2. Sealing member 22 is to be sealingly pierced by a needle as will be described below.

Figure 3:
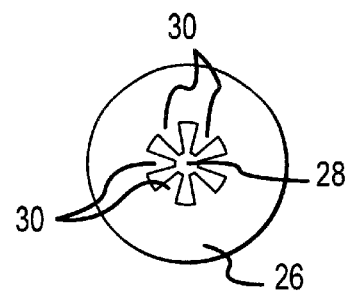
FIG. 3 is a bottom plan view of another isolated portion of the needle holding device FIG. 1.

A locking member 26 is also shown in FIG. I and more particularly in an isolated fashion in FIG. 3. As shown in more detail in FIG. 3, locking member 26 is a generally disc-shaped member having a central opening 28 and a plurality of protrusions 30 directed generally inwardly toward the central opening 28. Protrusions 30 are intended to engage a needle as will now be described in more detail relative to FIGS. 4A and 4B.

Figure 4A:
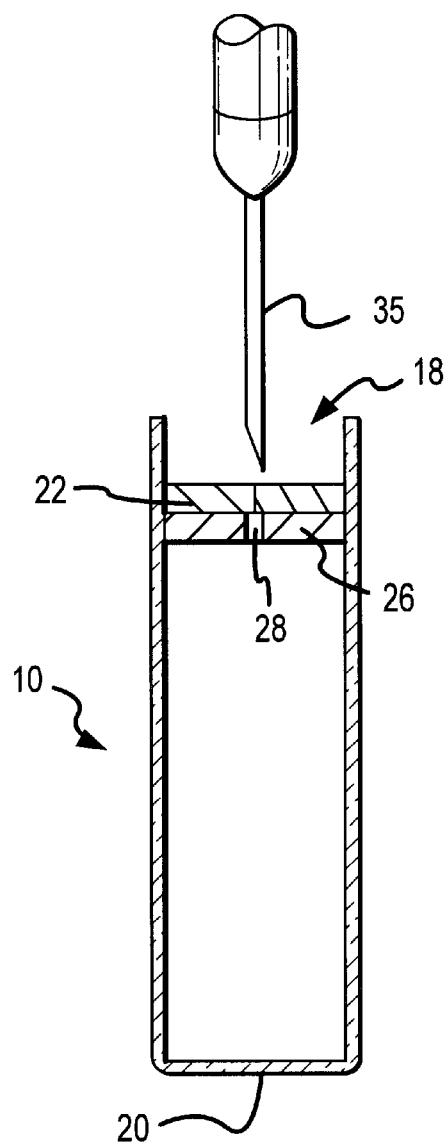
FIG. 4A is a cross-sectional view of the needle holding device of FIG. 1 with a needle to be inserted therein.
Figure 4B:
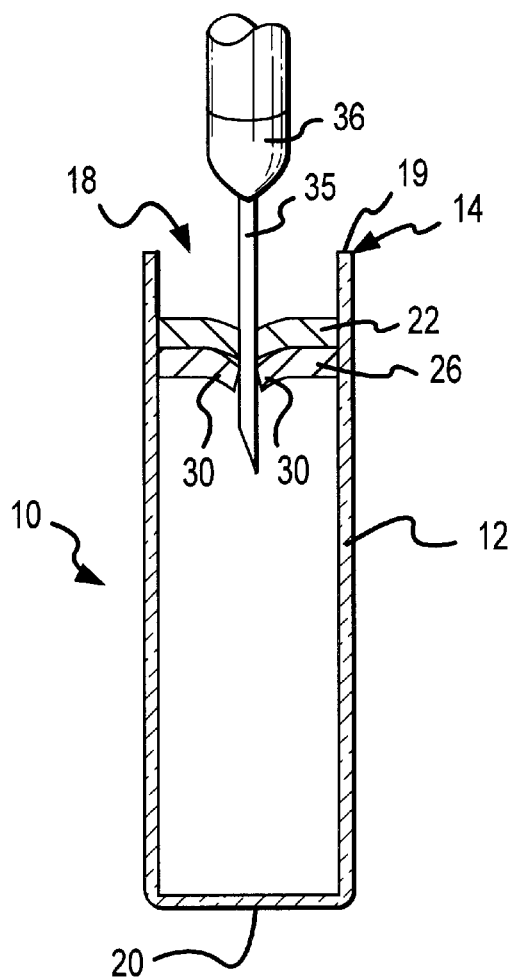
FIG. 4B is another cross-sectional view of the needle holding device of FIG. 1 with a needle inserted therein.

FIG. 4A shows a needle holding device 10 in operative position ready to admit a needle 35 therein through the opening 18 defined in the first end 14 thereof. As shown, needle 35 is poised to first pierce and penetrate the sealing member 22 and then proceed through the central opening 28 of the locking member 26. FIG. 4B shows the needle 35 after penetration into and through sealing member 22 and locking member 26. Sealing member 22 is shown exhibiting a slight deformation in response to the needle penetration, as does the locking member 26 although the deformation of the locking member is shown to be and may generally be more pronounced than that of the elastomeric sealing member 22. Note, the deformations shown in FIG. 4B may be slightly exaggerated, or could possibly be less than what may occur in actual practice. Even no deformation may be exhibited in certain circumstances. Further, it is preferable that if there is deformation in the locking mechanism 26, then only, or at least primarily, the protrusions 30 will deform downwardly in response to forced penetration of the needle into and through central opening 28. By deforming in this manner, protrusions 30 can grip the needle 35 to prevent its withdrawal from the holding device 10. This gripping may be frictional and/or include a jamming action of the tips of the protrusions 30 against and/or into the body of the needle 35 to restrain the needle within the holding device 10. This sort of protrusion deformation and frictional gripping or jamming is like that known and used by conventional lock washers employed to operatively lock nails or screws in place. Moreover, with appropriate locking member, protrusion and consequent aperture sizing relative to the needle to be held, this frictional gripping is highly secure against accidental withdrawal. As is known with conventional nail or screw lock washers, the initial insertion may proceed simply and with relatively little force, but after the protrusions are deformed and engaged with the inserted member (as shown in FIG. 4B), removal in the opposite direction will require a substantially greater force. Such a locking member will thus not release the inserted member absent the application of a removal force which is exceedingly large relative to the insertion force. This is what is meant by the words locked or held or the phrase non-releasably holding as used herein. A needle that is non-releasably held in a device of the present invention is not considered impossible to remove, merely removable only upon application of a force extraordinary to the otherwise normal circumstances of needle handling.

Moreover, a locking mechanism 26 as used herein may alternatively be spring-like in that the protrusions 30 may be deflected easily during insertion of the needle 35 into the locking mechanism 26, but in naturally tending toward their original position, the protrusions 30 may provide enhanced prevention of withdrawal. By tending toward their original positions, the protrusions 30 will provide a greater jamming force against the needle body and thus restrain removal of the needle 35. Provision of such action may preferably be obtained through use of metallic materials for the locking mechanism 26; however, plastics and other materials may also be used whether in the spring-like or mere frictional or jamming embodiments described herein.

Throughout this specification, use of directional terms such as upward or downward are merely intended to facilitate description relative to the embodiments shown in the attached drawings. Such descriptors are not intended to be limiting of the invention as it can easily be seen that other orientations will be operable as well. Thus, needles may as easily be inserted into and locked by holding devices having openings which face upwardly (as shown), or downwardly, transversely or in any other physical dimension.

FIG. 4B also shows implicitly a preferred alternative in which the first end opening 18 is defined diametrically wider than the needle hub 36 so that the large majority of needle 35 may be inserted into and through both the sealing and locking members 22, 26. When opening 18 is thus sufficiently wide, needle 35 may be inserted until hub 36 comes into contact with sealing member 22. An alternative to this which would present the same advantage even if the opening 18 is not wider than the hub 36 involves having the sealing member 22 disposed at or even above the opening 18 defined by first end 14 of the hollow body 12. Locking member 26 may also be moved closer to, or even superposed immediately above opening 18 as well. Moreover, it is foreseeable that locking member 26 may alternatively be superposed over sealing member 22, or even used without a sealing member 22. These and other alternative dispositions in adjacency to first end 14 are described in further detail below. Note, the use of a sealing member is preferred however, because its use together with a bottom wall 20 and impermeable body or sidewalls 12 will prevent the escape of blood from the interior of the device 10. Preventing this escape will then reduce exposure to bloodborne pathogens including numerous lethal viruses commonly associated with the risk of accidental needle sticks.

On the other hand, a preference for the slight recessing of the sealing and locking members 22, 26 a discrete distance downwardly as shown from the rim 19 of first end 14 is that the rim 19 may then better serve to catch and assist in guiding the needle into the respective openings in the sealing and locking members 22, 26. In this fashion, a needle may be brought first into contact with the rim 19 at a generally oblique angle (not shown), and then pivoted using rim 19 as a fulcrum until the point of the needle 35 is brought into proper position adjacent the locking member opening 28 for insertion thereinto and through. A wider mouthed body opening 18 is contemplated as well for this purpose as will be described further below. Thus, the diameter of rim 19 could be wider than the diameter of the hollow body generally at the location of the sealing and locking members 22, 26. Then, the hollow body could converge in a sort of funnel-shape down from the rim 19 to the sealing and locking members 22, 26. Both of these embodiments are intended to give the user greater facility in bringing the needle into position for insertion into the device 10. These are particularly helpful when the user is performing the needle insertion one-handed, such as when the user is using his or her other hand to apply manual pressure to the patient's vascular access site to provide hemostasis as described above.

It is preferred that device 10 be disposable so that once a needle 35 has been locked therein by engagement with the locking member 26, the needle 35 and device 10 can be disposed of without risk of exposing needle 35. A disposable device 10 can be and is preferably made from injection or blow molded plastic material. Sealing and locking members 22, 26 are then preferably subsequently fixed in place using an adhesive, glue, solvent or other bondant or perhaps by welding (e.g., ultrasonically, using radio-frequency (RF), or hot-plate welding), by employing retaining rings or by integrally molded seats or ridges, for example. In providing a preferably no-drip embodiment as described elsewhere herein, the sealing and/or locking members would preferably be connected so that one or the other of these members seals against the inner sidewalls 12 of device 10. Thus, a sealing member 22 may be attached in a fluid tight fashion like that apparently demonstrated in FIG. 1, for example, and then the connection of the corresponding locking member 26 would need not be fluid tight. Or, the locking member 26 may be affixed to the inner sidewalls in a fluid tight fashion and a sealing member 22 may then be connected in a fluid tight manner about the aperture 28 formed in locking member 26, and then the sealing member 22 would then not necessarily be connected in fluid tight relationship with the body 12 of device 10. Indeed, the sealing member 22 would not then even need to contact the body at all.

Moreover, substantially rigid and/or relatively flexible plastic materials are foreseeably usable for the body 12 depending mainly upon providing sufficient resiliency in coaction with the locking member 26 to retain a needle therein. Note, a partly flexible material may provide assistance at the rim 19 for catching and guiding a needle into proper insertion position. As mentioned, the sealing member 22 is preferably of an elastomeric material suitable for sealing around a needle to prevent fluid leakage therethrough. The locking member 26 is preferably of a metallic material, but plastics and other materials may be used as well.

The present invention is envisioned to be useful with any and all standard needles regardless of size or use. Thus, syringes or whole blood or winged needles or other medical sharps such as certain catheters or cannulas or other such implements may be locked in needle holding devices according to this invention and may then be disposed of without fear of accidental withdrawal. Certain locking member sizes may be useful to each adequately lock a plurality of various needle gauge sizes; although it may prove more beneficial to provide multiple sizes of devices 10 having various locking member interior aperture diameters to accommodate respective needle gauge sizes. Note, a large majority of dialysis procedures use needle sizes within a relatively small range of gauge sizes, as in gauge sizes 14 to 17, for example. It is thus foreseeable that in such situations, it is possible to present a single size locking mechanism to accommodate, grip and hold, most, if not all, needles within that range of sizes. Moreover, to provide greater security for adapting to needles within as well as those that may be outside of this range, for example, use of gauge sizes 12–13 and 18–20 are not uncommon; alternative or additional locking mechanisms may also be provided. The incorporation of additional mechanisms is described further below.

Figure 5:
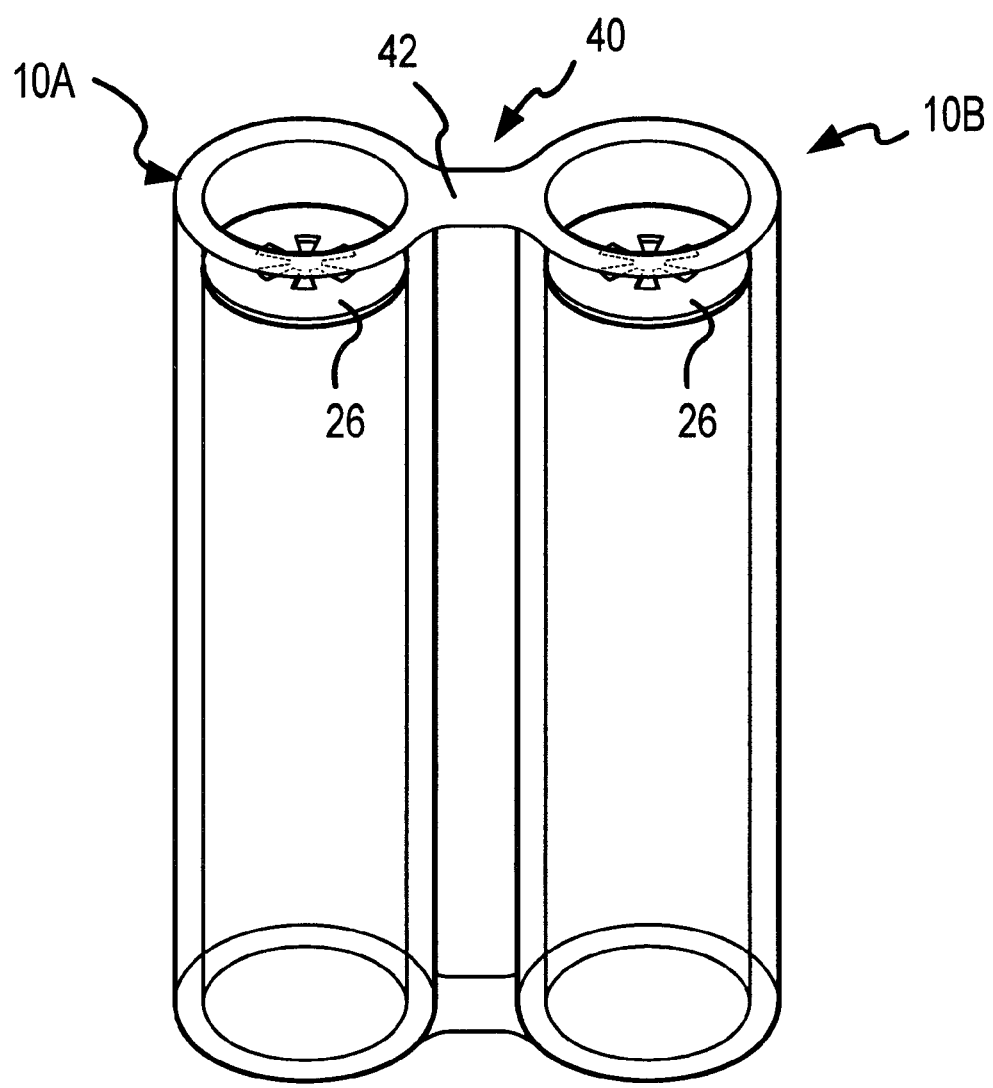
FIG. 5 is an isometric view of an alternative embodiment of a needle holding device according to the present invention.

A first alternative device embodiment is shown in FIG. 5. Here, a side-by-side arrangement 40 of two locking needle holding devices 10A and 10B is shown. Such a device may provide two alternative aperture sizes, or it may have greater applicability for use in medical procedures which often involve, if not require, the use of more than one needle. An example of this is in a two needle hemodialysis situation wherein both the patient access removal and return needles can be placed in a side-by-side device 40 after use. Side-by-side device 40 is preferably also a molded plastic disposable unit. Thus, a central connecting region 42 would preferably be molded simultaneously and integrally with each of the two holding devices 10A and 10B shown. Otherwise, two respective devices 10A and 10B may be attached together subsequent to initially separate molding to form a side-by-side device 40 using conventional technologies such as by using an adhesive, glue, solvent or other bondant, or by welding (ultrasonic, RF, or hot-plate, for example) or by employing other fastening means.

FIG. 5 shows still another alternative feature of the present invention briefly referred to above; namely, the use of a locking member 26 without a sealing member 22. As mentioned, it is preferred to include the sealing member for reasons of potential safety and/or cleanliness; i.e., to prevent the exit of blood drops from within the enclosed space of each device 10. However, a needle 35 will be fully and operably locked in a device 10 by engagement with a locking member 26 alone. Note, though shown and described relative to a side-by-side arrangement 40; this feature is fully adapted for use with any alternative device 10 described in this specification or any implicit equivalent or obvious extension hereof.

Figure 6:
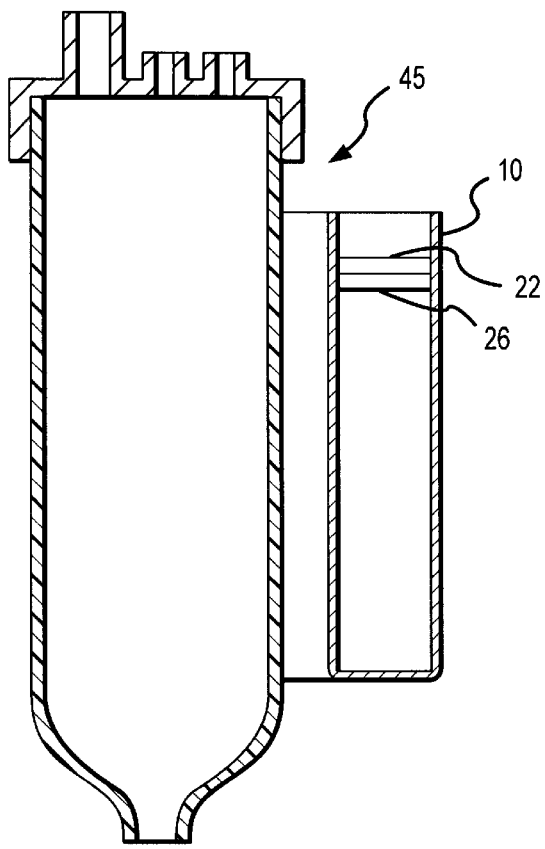
FIG. 6 is a cross-sectional view of another alternative embodiment of a needle holding device according to the present invention.

FIG. 6 shows a still further alternative embodiment in which the holding device 10 is integrally molded with or otherwise securely attached to an otherwise conventional drip chamber 45. Drip chambers such as this are known in the art of hemodialysis and like extracorporeal processes as injection or blow molded components of the disposable tubing sets which are attachable to the hemodialysis or other extracorporeal processing machines (not shown) for use. Usually, one or two drip chambers 45 are directly and rigidly connected to the machine during use. A needle holding device 10 connected to such a drip chamber 45 thus provides an easily and immediately accessible location for placing the needle upon removal from the patient. Being substantially rigidly connected to a drip chamber 45 which is, in turn, substantially rigidly connected to a processing machine (again, not shown) as is known in the art, the needle holding device 10 then provides a sturdy receptacle for the needle such that the needle can be easily inserted into device 10 using only one hand. This leaves the practitioner's other hand free for providing continued attention to the patient. As described, commonly, the practitioner uses one hand to apply pressure to the patient's needle access site to halt the bleeding at that point as understood for achieving hemostasis. The present invention allows the practitioner to continue to apply this pressure while simultaneously allowing the practitioner to deposit the needle in the needle holding device 10. Then, when the procedure is complete and all the needles are placed in respective needle holding devices, the entire tubing set including the one or more drip chamber(s) 45 and attached needle holding device(s) 10 are removed from the machine and disposed of. A closed blood loop may thus be formed for disposal as will be described in further detail relative to the embodiment of FIGS. 7 and 8, below.

Figure 7:
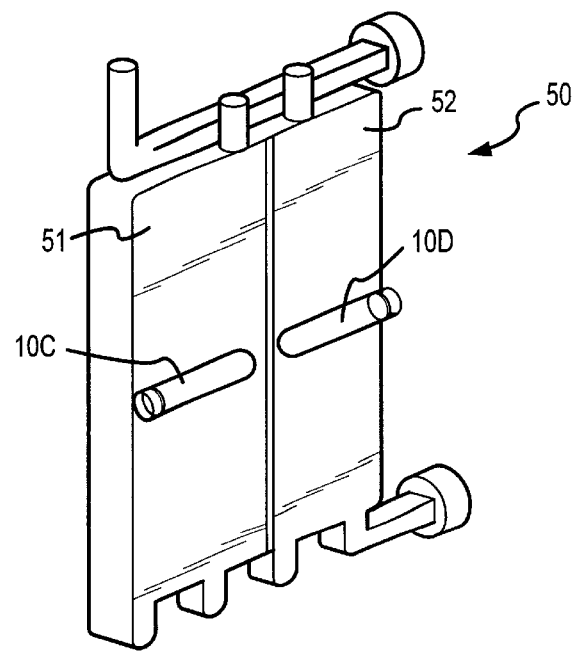
FIG. 7 is an isometric view of yet another alternative embodiment of a needle holding device according to the present invention.

FIG. 7 shows a modified form of drip chamber apparatus; namely, a dual drip chamber cassette 50. A cassette 50 according to this example is described in more detail in U.S. Pat. Nos. 4,666,598; and 4,770,787; inter alia, and is currently produced by GAMBRO Renal Care Products, Inc., a subsidiary of COBE Laboratories, Inc., both of Lakewood, Colo., USA, for use with COBE Centrysystem® 3 dialysis machines (C3™ machines), among others. Cassette 50 in FIG. 7 has been adapted to incorporate two needle holding devices 10C and 10D according to the present invention. These devices 10C and 10D are disposed on the front side of cassette 50 adjacent respective drip chambers 51 and 52 thereof. Drip chamber 51 is a venous drip chamber which temporarily holds blood received from a dialyzer (not shown) before it is circulated from there back to a patient. Drip chamber 52 is an arterial drip chamber which receives blood from the patient prior to being pumped to and through a dialyzer.

Figure 8:
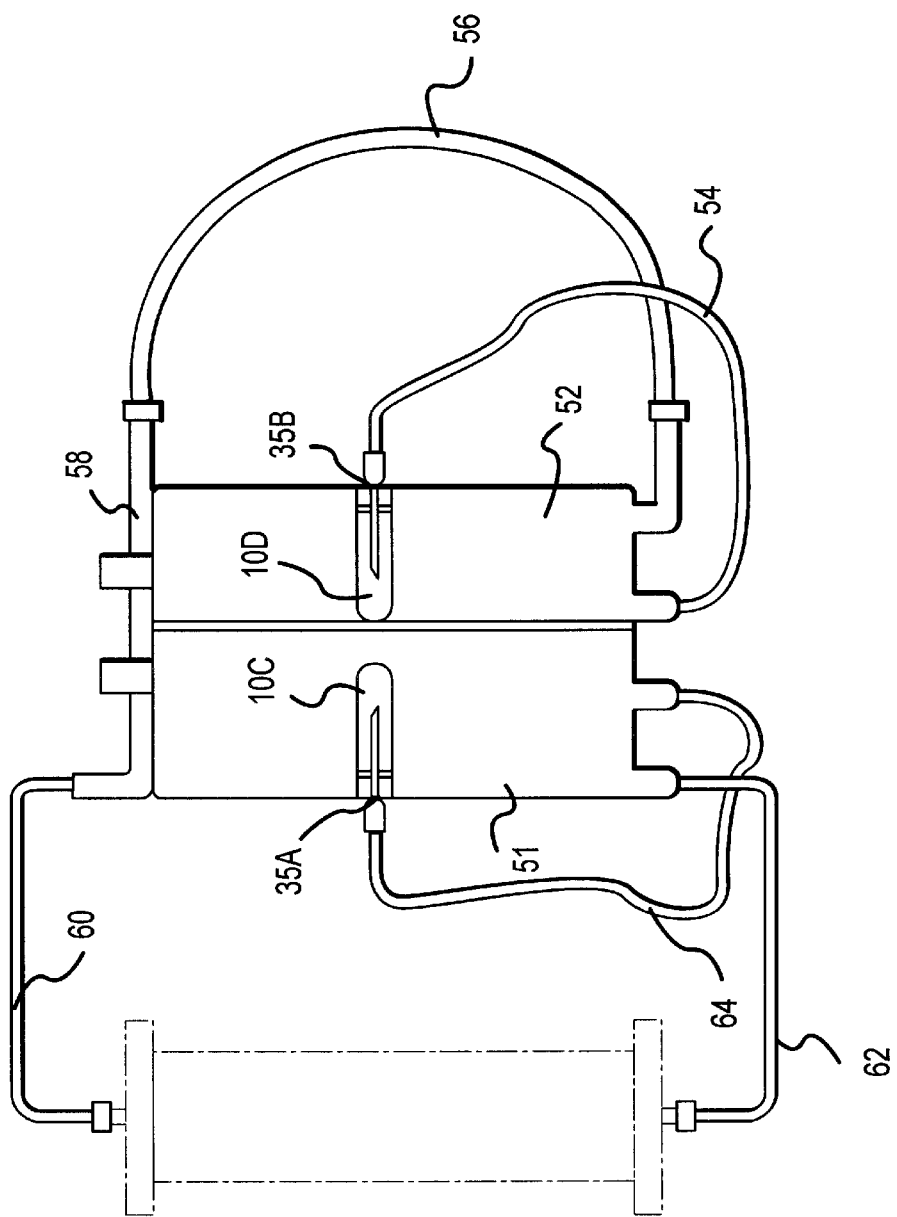
FIG. 8 is a front elevational view of the needle holding device of FIG. 7 shown in use with two needles locked in place according to the present invention.
Figure 17:
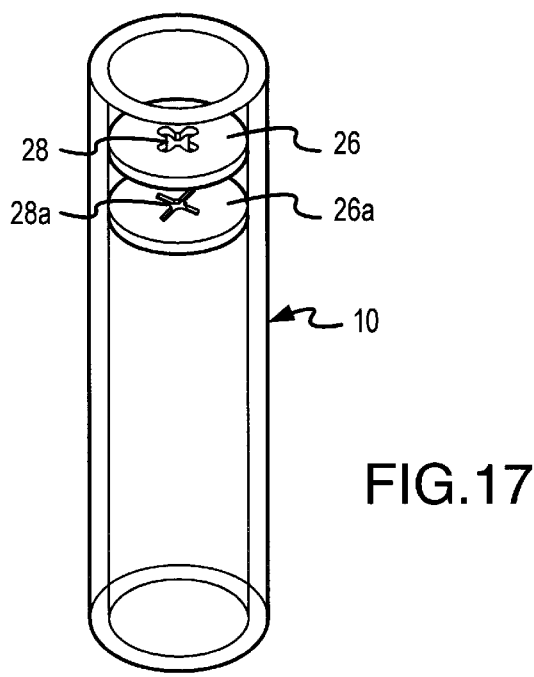
FIG. 17 is an isometric view of yet another alternative needle holding device according to the present invention.

Reference to FIG. 8 will clarify this description. In FIG. 8, the basic tubing elements of a disposable blood tubing set utilizing a cassette 50 have been added. Beginning in the lower right portion of the figure, a removal tubing line 54 is shown which provides for the withdrawal of blood from a patient which then flows to the arterial drip chamber 52. Blood in chamber 52 would then be pumped through tubing loop 56 by a peristaltic pump (not shown) to and through a top channel 58 connected to but superposed over chambers 51 and 52. Blood may then be made to travel through top channel 58 to a dialyzer inlet tubing line 60. Blood flowing through this line 60 would go into a dialyzer (shown in dashed lines in FIG. 8) or other extracorporeal blood processing device (not shown) and exit the dialyzer into an outlet line 62. This exiting blood may then flow back to cassette 50 into the venous drip chamber 51 from which it would then travel back to a patient through return line 64.

At the respective ends of return and removal lines 64 and 54 are respective blood return and removal needles 35A and 35B. During dialysis, needles 35A and 35B are disposed in the respective patient's vascular access return and removal sites for the purposes of removing blood from and returning blood to the patient. After use, these needles 35A and 35B may then be inserted in the respective needle holding devices 10C and 10D as shown in FIG. 8. With the needles 35A and 35B inserted as shown, then the cassette 50 and all of the tubing segments shown and described are simply disposable. The dialyzer or other extracorporeal processing device (not shown) is also preferably disposable as is known in the art. Thus, the arrangement shown in FIG. 8 including the dialyzer (in dashed lines) or other such device depicts an entirely disposable unit. And as shown, particularly when connected with a disposable dialyzer (or the like), the entire blood circuit is sealed in a closed loop for disposal. If sealing member(s) 22 are used in each of the holding devices 10C and 10D, then all the possible blood exits may/will be sealed off to totally prevent the escape of any blood from any point through the entire blood circuit. The sealed blood circuit thus reduces the risk of exposing anyone to potential blood-borne diseases as described hereinabove.

Devices 10C and 10D are shown connected to cassette 50 at relatively disparate locations, however, they may also be connected to cassette 50 in a fashion involving an arrangement like that shown in FIG. 5 such that the devices 10C and 10D are disposed next to and/or are connected to each other as a singular device 40. Other alternatives are also foreseeable. For example, devices 10C and 10D may alternatively be disposed in upright vertical orientations instead of the horizontal dispositions shown. The horizontal positions may, however, provide better access to the user while the user is continuing to provide attention to the patient. Also, one or more devices 10 may be connected to other blood tubing set components; pressure pods, access sites or tubing connectors, for example, or directly to one or more tubing segments. In any of these cases, the devices 10 may be separately formed (molded or otherwise) and then connected to the tubing set component or tubing segment (using, as above, a bondant, a welding technique or other mechanical fastening means) or could be integrally formed with the respective component or tubing segment such as by injection or blow molding or the like.

Other additional alternative embodiments will now be described with particular reference to FIGS. 9–19, noting however, that the scope of alternatives is not limited to those explicitly described here. Rather, the scope of the present invention is intended to also encompass those other equivalents not explicitly described yet which would be properly understood as providing the functional features hereof toward the ends taught herein.

With respect first to FIGS. 9–15, several alternative locking mechanisms 26 are shown which may be used in a locking device 10 according to the present invention. FIGS. 9 and 10 show an alternative mechanism 26 which demonstrates in greater detail a protrusion deformation as introduced in the description of FIG. 4B, above. In this case, only two protrusions 30 deform when engaging needle 35. Dashed lines in FIG. 10 indicate the most probable lines of bending or hinge-like action when engaged by a needle 35 as shown in FIG. 9. These may even be lines of weakness preformed therein to dictate the bending action. Note, as above, these protrusions 30 may also exhibit a spring-like tendency to return to their normal disengaged position to thereby impose a greater restraining or jamming force against removal of the needle 35. The FIGS. 9 and 10 embodiment also shows a sort of substantially rigid support opposite the bending protrusions 30, against which the needle 35 can be jammed or otherwise forced by the deformed protrusions 30. This coaction may provide an enhanced needle holding force and may be further strengthened depending upon the spring force of the protrusions, if any. Note also the sharp edge of the protrusion 30 shown in FIG. 9 in contact with the needle body 35. This sharp edge may actually dig into the needle body 35 thus providing a still further obstacle to removal. Any or all of these features may be found in any or all of the alternative embodiments described herein or otherwise encompassed within the scope of this invention.

FIGS. 11 and 12 demonstrate two further alternative embodiments presenting first more and then fewer protrusions. There are four such protrusions 30 in FIG. 11 and perhaps none in FIG. 12. Nevertheless, the mode of operation will be the same for each although it will be the sides of the opening in FIG. 12 rather than the ends of discrete protrusions which will grip the needle once inserted therein. Thus, a mere aperture with no protrusions and perhaps little or no bending or other deformation may be operable as may an aperture coacting with one or any practical number of protrusions.

FIGS. 13 and 14 demonstrate an alternative embodiment in which the protrusions 30 are pre-formed to be disposed at a slight angle relative to the remainder of the locking mechanism 26. The slight angle may provide the protrusions 30 with an enhanced restraining force. This slightly angled enhancement may be available with spring-like or non-spring-like protrusions 30. The preferred mode of use of a locking mechanism 26 having pre-bent protrusions 30 would be to insert the needle 35 into the mechanism 26 such that the needle 35 follows the pre-bent orientations of the protrusions 30, and would oppose these orientations in an attempted withdrawal. Referring to FIGS. 13 and 14, this would mean inserting the needle in an upward direction from the bottom to follow the upward pre-bent orientations shown. Then, an attempted withdrawal would tend to pull the protrusions toward a flatter disposition which would be contrary to the natural spring-like tendency of spring-like embodiments and/or would otherwise serve to create a narrower opening even in non-spring-like embodiments which would cause further restriction on the possibility for removal of the needle 35 therefrom. The upwardly bent protrusions are shown in this fashion for ease of drawing depiction and are not intended to intimate a limitation to this direction. Indeed, downward bent protrusions would likely be preferred for use in most of the respective device orientations of the alternative needle holding devices 10 shown and described herein. Thus, a needle would be inserted downwardly in such embodiments following downward pre-bent protrusions which would restrict upward and outward removal.

Figure 16:
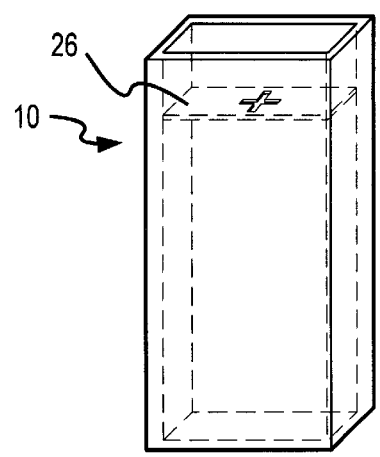
FIG. 16 is an isometric view of an alternative needle holding device according to the present invention.

FIG. 15 depicts a quadrilaterally-shaped locking mechanism 26 presented here to demonstrate that alternative embodiments of device 10 need not be circular in cross-section. Indeed, any shape may be used for a locking mechanism 26 and consequently also for a device 10, the only requirement being a necessity of size and/or shape adequate to contain the needle once inserted therein. The quadrilaterally-shaped locking mechanism 26 of FIG. 15 is similar to that disposed in the alternative needle holding device 10 shown isometrically in FIG. 16; this device 10 having a substantially quadrilaterally-shaped cross-section (not separately shown) matching that of the locking mechanism 26 disposed therein. Substantially rectangular or square shapes are shown in FIGS. 15 and 16; however, the scope of the present invention should not be so limited here either as described above.

Although introduced generally above, three still further alternative embodiments are shown in the attached drawings. First, in FIG. 17, a device 10 is shown having two locking mechanisms 26, and 26*a* disposed therein. The respective openings 28, and 28*a* are of different sizes to accommodate differently sized needles to be disposed therein. Thus, in the FIG. 17 example, a smaller needle (not shown) may be passed through the aperture 28 of the upper locking mechanism 26 without being fully engaged with the protrusions thereof, but may then pass into and through the aperture 28*a* of the second locking mechanism 26*a* and then be properly engaged with the protrusions thereof and locked or non-releasably held in place in the holding device 10. Note, the separation distance shown between the respective locking mechanisms 26, 26*a* may be as shown, or larger, or smaller depending upon user or manufacturer choice. Thus, they may be made to abut each other or to provide a discrete distance therebetween which may be used to accommodate distinct needle lengths as well as gauge/width sizes. Additionally, any practical number more than two locking mechanisms could also be used in a device 10. Nevertheless, as mentioned above, it is also foreseeable that a single locking mechanism 26 could be used to accommodate the more prevalent needle sizes occurring in dialysis and like extracorporeal blood processing procedures.

Figure 18:
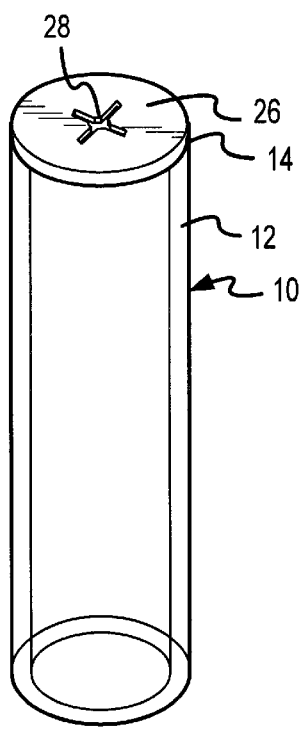
FIG. 18 is an isometric view of still another alternative needle holding device according to the present invention.

FIG. 18 likewise depicts an alternative embodiment introduced above. In FIG. 18, the locking mechanism 26 is shown disposed on the first end 14 outside of the hollow body 12 of device 10. Though this embodiment was introduced hereinabove, the prior drawing figures have to this point all depicted the locking mechanism as disposed inside the interior chamber of the hollow body 12. This FIG. 18 embodiment may provide advantages in manufacturability, for example in ease of affixation (by gluing, welding or otherwise as described above) of locking mechanism 26 on as opposed to inside the first end 14; or also possibly in use, such as by making the aperture 28 readily accessible to the user. A similar yet unshown alternative embodiment might present the locking mechanism 26 disposed inside the side walls 12 yet disposed substantially at the uppermost edge of the first end 14 to provide a device 10 very similar to that shown in FIG. 18. Nevertheless, in all of the embodiments described in this specification, the locking mechanism 26 is described as preferably disposed adjacent the first end 14 regardless whether the locking mechanism 26 is disposed outside the hollow body 12 as shown in FIG. 18, or whether it is disposed inside the hollow body 12 immediately at the first end. 14 or disposed a discrete distance inside and below the first end. Adjacent in this specification is intended to mean close to or at the first end and includes all of these embodiments.

Similarly, a sealing member 22 (not shown in FIG. 18) may also be disposed outside or inside the body side walls 12. Preference may here as well depend on either manufacturability or usability. It is also foreseeable that the sealing member 22 could be disposed so as to contact only the locking mechanism 26 and not contact the body 12 as for example if it were positioned on and connected to the exteriorly disposed locking mechanism 26 shown in FIG. 18. Note, a non-contacting sealing member 22 could also be envisioned on an innerly-disposed locking member 26 as mentioned above as well. Also, the sealing member 22 may be disposed underneath the locking member 26 whether it contacts the body 12 (via the rim 19 or the innerwalls thereof), or the locking member 26 or both.

Figure 19:
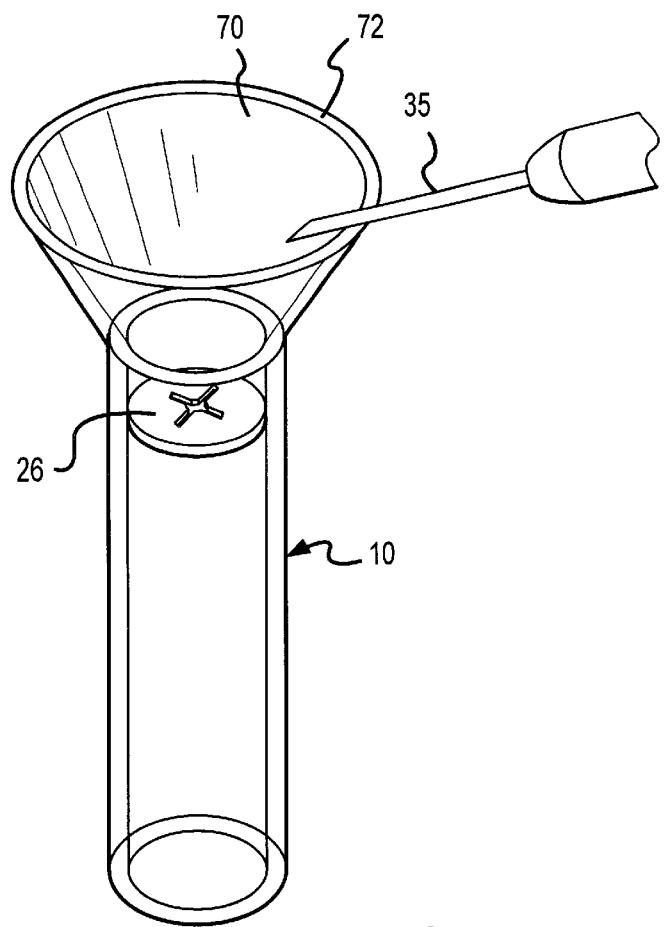
FIG. 19 is an isometric view of yet still another alternative needle holding device according to the present invention.

Another alternative is shown in FIG. 19 in which a sort of funnel-shaped guide member 70 has been added to a device 10. Guide member 70 is preferably usable, as shown, to provide assistance in guiding a needle into proper insertion position. First, needle 35 can be made to come into contact with the lip 72 of guide member 70 as shown, and from there be simply maneuverable down toward the locking mechanism 26 for insertion therein as described throughout this specification. Thus, insertion may be made simpler, surer and perhaps safer, particularly by a user using only one hand. As described above, such a user can then continue to use his or her other hand to provide pressure to the patient's vascular access site and thereby achieve hemostasis. Note, as introduced above, such a guide member 70 may be considered an extension and or mere widening of the first end 14 of a device 10, wherein the rim 19 of the FIGS. 1, 4A and 4B embodiment would provide this same functionality. This is not to say that a user could not also use a guided functionality with a top-mounted (FIG. 18) or interior but topmost mounted locking mechanism 26. Rather, the user would then use the exterior edge of the locking mechanism or the rim 19 to initially catch the needle body 35 before maneuvering the needle into position for insertion. Moreover, funnel-shaped guide members such as member 70 could also be incorporated on any or all embodiments described explicitly herein or implicitly equivalent hereto. Quadrilaterally or otherwise multi-sided and/or shaped funnel type guide members could be incorporated on non-circular alternative embodiments such as that shown in FIG. 16, for example, or may need to be superposed over an exteriorly mounted locking mechanism 26 like that shown in FIG. 18. Eccentric (non-circular) or flattened on one side mouth shapes may be required on cassette or drip chamber mounted needle holding devices, the flattened side being adjacent the drip chamber or cassette. Note also that the lip 72 and/or the guide member 70 may be partly or entirely flexible as this may enhance the catch and guide functions thereof. This may then follow the preference of consistency of the other components of device 10 which as described may as well be rigid or flexible as desired so long as they sufficiently coact to retain a needle inserted therein.

Accordingly, a new and unique invention has been shown and described herein which achieves its purposes in an unexpected fashion. Numerous alternative embodiments readily foreseeable by the skilled artisan, which were not explicitly described herein are considered within the scope of the invention which is limited solely by the claims appended hereto.

What is claimed is:

1. A needle holding device comprising:
   an elongated hollow body having first and second ends, said first end being substantially open for receiving a needle inserted therein;
   a looking member operably connected to said hollow body, said locking member being disposed adjacent said first end of said hollow body, and said locking member having an opening defined therein to receive and non-releasably hold a needle inserted therein; and
   an elastomeric sealing member operably connected to said hollow body, said elastomeric sealing member being connected to said hollow body adjacent said first end of said hollow body, said elastomeric sealing member being adapted to sealingly admit a needle pierced therethrough.

2. A needle holding device according to claim 1 in which said locking member is disposed inside the hollow body adjacent the first end thereof.

3. A needle holding device according to claim 1 in which said locking member is disposed inside the hollow body a discrete distance from yet still adjacent the first end thereof.

4. A needle holding device according to claim 1 in which said locking member is disposed outside of yet is still connected to the hollow body adjacent the first end thereof.

5. A needle holding device according to claim 1 which comprises a plurality of locking members operably connected to said hollow body, said plurality of locking members being disposed adjacent said first end of said hollow body, and said locking members each having an opening defined therein to receive and non-releasably hold a needle inserted therein.

6. A needle holding device according to claim 1 in which said second end of said hollow body is closed.

7. A needle holding device according to claim 1 in which said device further comprises a closure portion connected to said second end of said hollow body such that said closure portion renders said second end closed.

8. A needle holding device according to claim 1 in which said locking member has one or more protrusions directed inwardly toward said opening defined in said locking member, said one or more protrusions being adapted to engage a needle in a non-releasable holding relationship when such a needle is inserted into the opening defined in said locking member.

9. A needle holding device according to claim 8 in which said one or more protrusions frictionally engage a needle inserted therein, the frictional engagement providing the non-releasable holding relationship which restrains the needle within the needle holding device.

10. A needle holding device according to claim 8 in which said one or more protrusions jam against a needle upon engagement with the needle when such a needle is inserted into the opening defined in said locking member, this jamming engagement providing the non-releasable holding relationship which restrains the needle within the needle holding device.

11. A needle holding device according to claim 8 in which said one or more protrusions deform upon engagement with a needle when such a needle is inserted into the opening defined in said locking member.

12. A needle holding device according to claim 8 in which said one or more protrusions have a spring action in which the one or more protrusions may deform upon engagement with a needle when such a needle is inserted into the opening defined in said locking member, the spring action providing a tendency for said one or more protrusions toward returning to their undeformed state, this spring action providing the non-releasable holding relationship which restrains the needle within the needle holding device.

13. A needle holding device according to claim 8 in which said locking member also has a rigid support surface with which a needle inserted therein will also come into contact, said one or more protrusions coacting with said rigid support surface upon engagement with a needle inserted therein to provide the non-releasable holding relationship which restrains the needle within the needle holding device.

14. A needle holding device according to claim 8 in which said one or more protrusions are pre-bent at a slight angle, yet still being adapted to engage a needle in a non-releasable holding relationship when such a needle is inserted into the opening defined in said locking member.

15. A needle holding device according to claim 1 in which said elastomeric sealing member is a solid piece of pierceable elastomeric material.

16. A needle holding device according to claim 1 in which said elastomeric sealing member has a slit formed therethrough.

17. A needle holding device according to claim 1 in which said hollow body is formed of a plastic material.

18. A needle holding device according to claim 17 in which said hollow body is injection molded.

19. A needle holding device according to claim 17 in which said hollow body is blow molded.

20. A needle holding device according to claim 1 in which the elongated hollow body thereof is a first hollow body, the needle holding device further comprising:
   a second hollow body connected to said first hollow body, said second hollow body having first and second ends, said first end of said second hollow body being substantially open for receiving a needle inserted therein; and
   said second hollow body also having a second locking member operably connected to said second hollow body, said second locking member being disposed adjacent said fit end of said second hollow body, said second locking member having an opening defined therein to receive and non-releasably hold a needle inserted therein.

21. A needle holding device according to claim 20 in which said second hollow body also has a second elastomeric sealing member operably connected to said second hollow body, said second elastomeric sealing member being connected to said second hollow body adjacent said first end of said second hollow body, said second elastomeric sealing member being adapted to sealingly admit a needle pierced therethrough.

22. A needle holding device according to claim 20 in which said second end of said second hollow body is closed.

23. A needle holding device according to claim 20 in which said second locking member has one or more protrusions directed inwardly toward said opening defined in said second locking member, said one or more protrusions being adapted to engage a needle in a locking relationship when the needle is inserted through the opening defined in said second locking member.

24. A needle holding device according to claim 1 in which the elongated hollow body is connected to a tubing segment.

25. A needle holding device according to claim 1 in which the elongated hollow body is connected to a tubing set component.

26. A needle holding device according to claim 25 in which the tubing set component is a pressure pod.

27. A needle holding device according to claim 25 in which the tubing set component is an access site.

28. A needle holding device according to claim 25 in which the tubing set component is a tubing connector.

29. A needle holding device according to claim 1 in which the elongated hollow body is connected to a drip chamber.

30. A needle holding device according to claim 1 in which the elongated hollow body is connected to a dual drip chamber cassette.

31. A needle holding device according to claim 30 in which a second elongated hollow body is also connected to the dual drip chamber cassette; said second hollow body having a first open end and a second locking member operably connected to said second hollow body, said second locking member being disposed adjacent said first open end of said second hollow body, said second locking member having an opening defined therein to receive and non-releasably hold a needle inserted therein.

32. A needle holding device according to claim 1 which further comprises a needle guide member connected to said first end of said hollow body.

33. A needle holding device according to claim 32 in which said needle guide member is a substantially funnel-shaped member.

34. A method for disposing of medical needles after use, said method comprising the steps of:
   inserting a needle into a needle holding device, said needle holding device having an elongated hollow body with first and second ends, said first end being substantially open for receiving a needle inserted therein, and a locking member operably connected to said hollow body, said locking member being disposed adjacent said first end of said hollow body, and said locking member having an opening defined therein to receive and non-releasably hold a needle inserted therein; and
   disposing of the needle and the needle holding device simultaneously with said needle non-releasably held inside said needle holding device;
   wherein said needle is connected to a blood tubing set and said blood tubing set is disposed of simultaneously with said needle and said needle holding device.

35. A method according to claim 34 in which said blood tubing set is connected to a disposable blood processing apparatus and said blood processing apparatus and said blood tubing set are disposed of simultaneously with said needle and said needle holding device.

36. A method according to claim 35 in which said blood processing apparatus is a dialyzer.

37. A needle holding device comprising:
   an elongated hollow body having first and second ends, said first end being substantially open for receiving a needle inserted therein;
   a locking member operably connected to said hollow body, said locking member being disposed adjacent said first end of said hollow body, and said locking member having an opening defined therein to receive and non-releasably hold a needle inserted therein; and
   wherein the elongated hollow body is connected to a tubing set component.

38. A needle holding device according to claim 37 in which the tubing set component is a tubing segment.

39. A needle holding device according to claim 37 in which the elongated hollow body is connected to a drip chamber.

40. A needle holding device according to claim 37 in which the elongated hollow body is connected to a dual drip chamber cassette.

41. A needle holding device according to claim 40 in which a second elongated hollow body is also connected to the dual drip chamber cassette; said second hollow body having a first open end and a second locking member operably connected to said second hollow body, said second locking member being disposed adjacent said first open end of said second hollow body, said second locking member having an opening defined therein to receive and non-releasably hold a needle inserted therein.

42. A needle holding device according to claim 37 in which the tubing set component is a pressure pod.

43. A needle holding device according to claim 37 in which the tubing set component is an access site.

44. A needle holding device according to claim 37 in which the tubing set component is a tubing connector.

* * * * *